(12) United States Patent
Almarhoon et al.

(10) Patent No.: US 11,610,659 B1
(45) Date of Patent: Mar. 21, 2023

(54) TAMPER-PROOF MEDICINAL DRUG CONTAINER HAVING CONTENT-DESTRUCTION MECHANISM

(71) Applicant: ABP Industries LLC, Chicago, IL (US)

(72) Inventors: Aqeel Ali Almarhoon, Chicago, IL (US); Benjamin K. Herrington, Chicago, IL (US)

(73) Assignee: ABP Industries, LLC, Chicago, IL (US)

( * ) Notice: Subject to any disclaimer, the term of this patent is extended or adjusted under 35 U.S.C. 154(b) by 8 days.

(21) Appl. No.: 17/403,042

(22) Filed: Aug. 16, 2021

(51) Int. Cl.
  *G16H 20/13* (2018.01)
  *A61J 7/04* (2006.01)

(52) U.S. Cl.
  CPC ............ *G16H 20/13* (2018.01); *A61J 7/0418* (2015.05); *A61J 7/0445* (2015.05)

(58) Field of Classification Search
  CPC ........ G16H 20/13; A61J 7/0418; A61J 7/0445
  See application file for complete search history.

(56) References Cited

U.S. PATENT DOCUMENTS

| | | | | |
|---|---|---|---|---|
| 7,392,918 B2* | 7/2008 | Holloway | ................. | A61J 1/03 221/277 |
| 10,512,592 B1* | 12/2019 | Sandhu | ................. | G07F 11/005 |
| 2008/0251530 A1* | 10/2008 | Holloway | ............. | A61J 7/0076 700/231 |
| 2009/0223994 A1* | 9/2009 | Getz | ................. | B65D 83/0427 221/154 |
| 2014/0214200 A1* | 7/2014 | Chrusciel | ............. | A61J 7/0076 221/15 |
| 2015/0347713 A1* | 12/2015 | Seeger | ..................... | A61J 7/02 700/236 |
| 2016/0158107 A1* | 6/2016 | Dvorak | ................. | A61J 7/0007 221/9 |

* cited by examiner

*Primary Examiner* — Michael Collins
(74) *Attorney, Agent, or Firm* — Harbin & Hein PLLC (57) ABSTRACT

A tamper-proof container for medication that enables self-destruction of contents upon tampering comprising an outer housing having a lid that permit insertion of pills, an inner medication chamber for holding discrete quantities of said pills, a dispensing section to provide timed dispensing of pills from said inner medication chamber according to a timing device preprogrammed according to a dosage regime, a pill destruction section to destroy and/or adulterate said pills upon activation, a pressurized double-walled bladder forming an annular chamber surrounding the medication chamber, and medication destruction section being operative to depressurize and activate destruction of pills upon tampering with the device.

5 Claims, 11 Drawing Sheets

TAMPER-PROOF MEDICINAL DRUG CONTAINER HAVING CONTENT-DESTRUCTION MECHANISM

This invention claims the benefit of U.S. Provisional Application Ser. No. 63/067,796 filed Aug. 19, 2020 in the name of the same inventors hereof.

BACKGROUND

This invention concerns tamper-proof containers, but more specifically to a tamper-proof container having a content-destruction mechanism.

It is widely accepted that (a) certain Rx drugs are abused including, without limitation, opioids, (b) the misuse, abuse, addiction and diversion potential of Rx drugs, particularly opioids, have been identified as the proximate cause of the ongoing illicit heroin and synthetic heroin crises currently ravaging the US, and (c) currently, the only available access limiting/risk mitigation/harm reduction tools available to physicians respecting these drugs are (i) to limit prescriptions and/or (ii) to prescribe these medications (i) with less than the desired/effective (frequency and dosage) amounts and (ii) only to patients who are seen at lower risk of subsequently presenting with the problems identified in (b) above. However, given the risks inherent in these drugs, and especially in opioids, these options are often insufficient. Many patients may easily circumvent limits on Rx frequency and dosage given the existing market standard prescription medication bottle, thereby subjecting themselves and persons in their immediate proximity (i.e., household members, family, friends, caretakers and visitors) to significantly increased risk of misuse, abuse, addiction, overdose and even death. Thus, easy access to opioid medications is identified as the root cause of the national opioid crisis and problem. Certain other commonly prescribed Scheduled and Non-Scheduled prescription medications also carry inherent risks much like opioids.

To address this problem, the present invention is designed to increase patient adherence t to medication dosage while simultaneously reducing the risk of patient or $3^{rd}$ party misuse, abuse, addiction, diversion, overdose, injury or death inherent in the dispensation of these medications. The present invention comprises a medication dispensing device, which includes a way to regulate dosage, frequency and patient (or $3^{rd}$ party) access outside of the prescribed prescription parameters.

SUMMARY OF THE INVENTION

A tamper-proof container for medication that enables self-destruction of contents upon tampering or expiration comprising an outer housing having a lid that permits insertion of pills, an inner medication chamber for holding discrete quantities of said pills, a dispensing section to provide timed dispensing of pills from said inner medication chamber according to a timing device preprogrammed according to a dosage regime, a pill destruction section to destroy or adulterate said pills upon activation, a pressurized double-walled bladder forming an annular chamber surrounding the medication chamber, and medication destruction section being operative to depressurize and activate destruction of pills upon tampering with the device.

Other features of the invention include a pre-loaded coil spring that spins a shaft to effect destruction by grinding of pills, release of a substance (either an FDA approved generic opioid antagonist, in the case of opioids, and/or in case of non-opioid medication, a non-toxic aqueous suspension containing medication adsorbents (activated charcoal), surfactants (soap), anti-freezing compounds (sorbitol, propylene glycol), and/or sensory deterrents (sulfur, capsaicin)) to counteract the effects post-ingestion, render inert, adsorb] and/or adulterate the medication with a foul taste, color, odor or other undesirable property to deter consumption by a user, and/or mixing the ground medication contents therewith.

Other aspects, features and embodiments will become apparent upon review of the following description taken in connection with the accompanying drawings. The invention, though, is pointed out by the appended claims.

DETAILED DESCRIPTION

Figure 1:
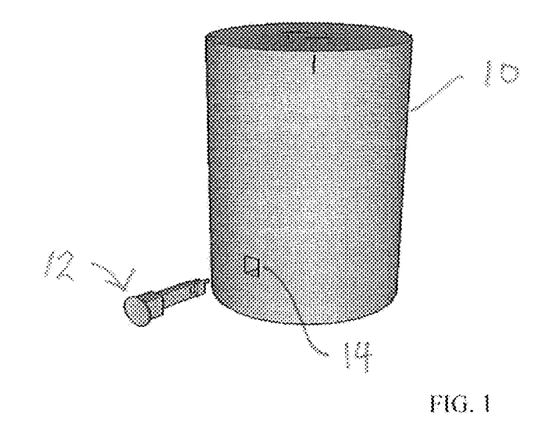
FIG. 1 is a perspective view of an exemplary tamper-proof container.

FIG. 1 is a perspective exterior view of an exemplary tamper-proof container 10 according to an aspect of the present invention, which includes a dispensing key 12 adapted for insertion through an orifice 14 of container 30 in order to retrieve a pill.

Figure 2:
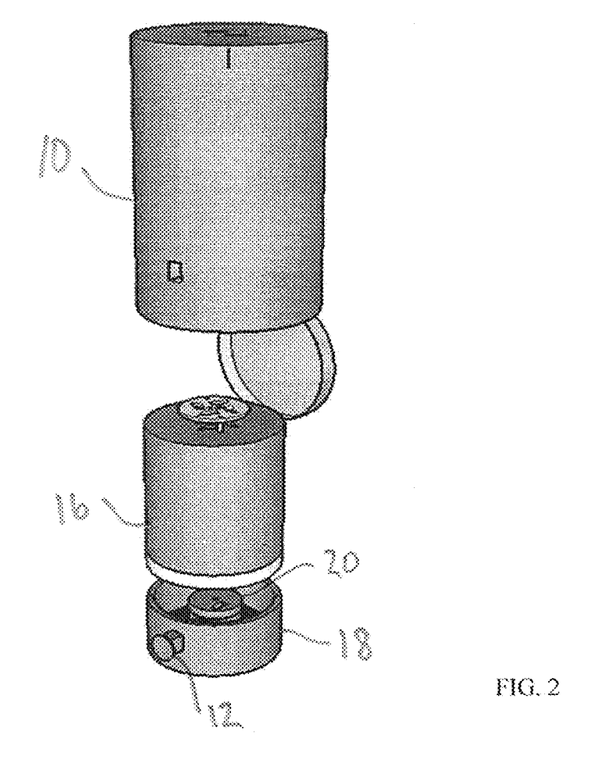
FIG. 2 in an exploded view of the tamper-proof container of FIG. 1.

FIG. 2 is an exploded view of the tamper-proof container 10 of FIG. 1 comprising an expandable/collapsible bladder 16 which may comprise a translucent lid at the bottom inside outer casing 10 and a dispensing section 18 having an internal dispensing mechanism 20, subsequently described. Bladder 16 forms an air-pressurized double-walled annular chamber enveloping the medicinal contents and may comprise rubber or material having similar properties. Locking key 12 includes conductive circuit elements that control a latching/locking functionality (subsequently described). Container 10 also includes four small tablet-sized slits on top surface that enables insertion of medication into the interior of the device (by retail pharmacist or manufacturer, for example).

Kevlar fabric (or similarly puncture, pierce and cut resistant material, which also increases the structural integrity/strength of the material to which it is bonded) may be bonded to entirety of assembled components excepting the four medication loading slits on the top surface of the device, the key slot and/or the bottom quarter of the device in order to provide additional strength beyond cutting, sawing, piercing, penetration, heating, chemical attack, compressive forces, catastrophic destruction of the encasement, and which will provide further time between breach of encasement and activation of anti-tampering air bladder or catastrophic failure due to external application of force that permits the medication to combine with the naltrexone tablets and a proprietary non-toxic admixture of activated charcoal, sorbitol, kaolin clay, sensory deterrent and possibly, a surfactant.

Figure 3A:
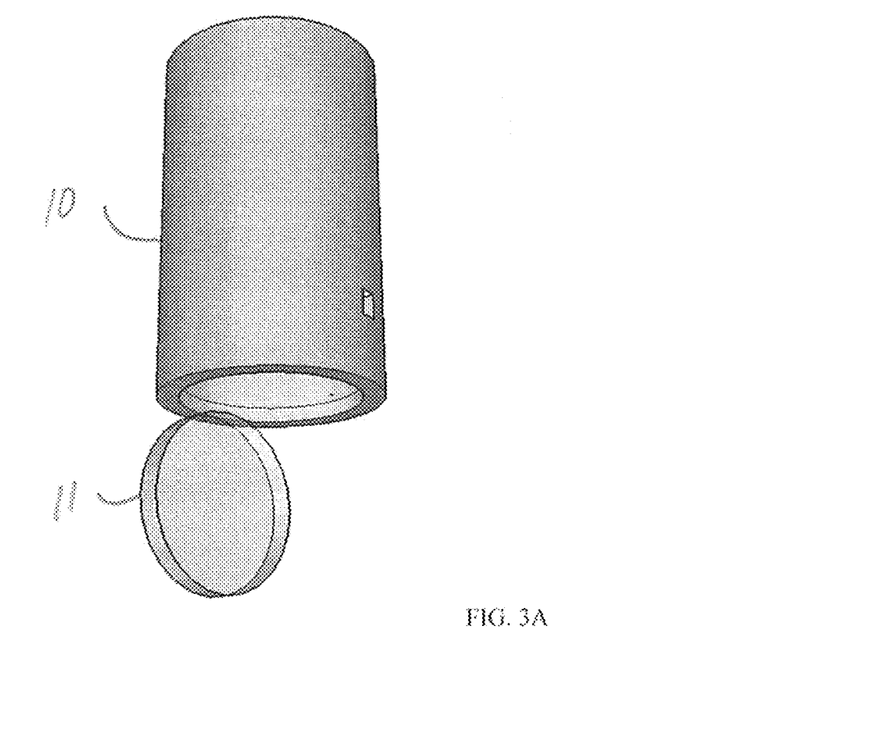
FIG. 3A shows a perspective view of a tamper-proof container together with encasement lid.

FIG. 3A shows a perspective view of container 10 together with encasement lid 11, which are shown as one connected piece to provide view of connection required to preserve the integrity of the pressurized air bladder anti-tamper mechanism which will be bonded to the interior walls/surfaces.

Figure 3B:
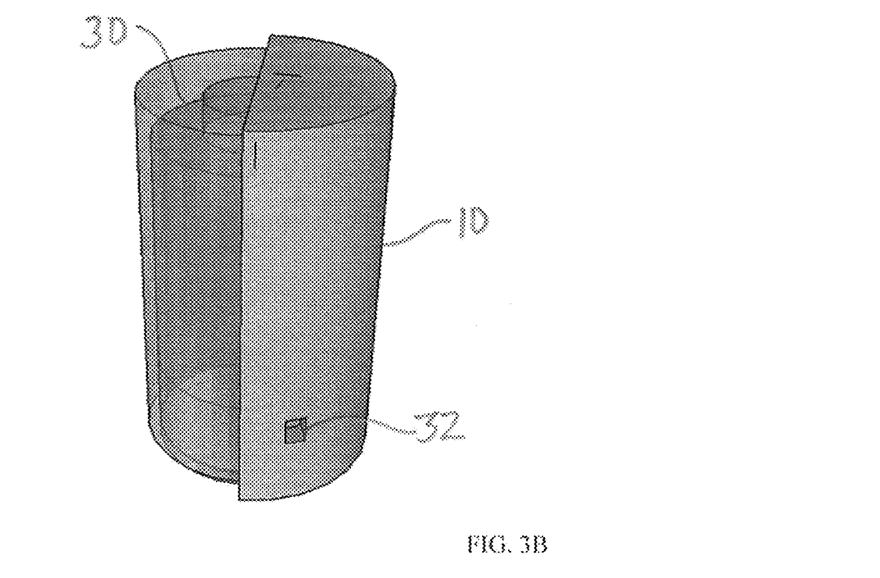
FIG. 3B shows a cut-a-way view of a container showing medication dispensation opening at bottom quarter of device.

FIG. 3B shows a partial cut-a-way view of container 10 showing medication dispensation opening at bottom quarter of device and revealing the encased/bonded pressurized air bladder 30. The air bladder 30 is a single continuous piece with no holes or openings that would allow air to escape. It does, however, have four slits at top and an opening on the side. These have no bearing on the air pressure inside the bladder.

Pressurized air bladder 30 is double-walled and forms an "annular" pressurized air space surrounding/enclosing an internal chamber that contains the medicinal tablets or pills. And only the annular space is pressurized—not the internal chamber. This way, a non-compliant patient must to go through the double-walled air bladder first to reach the pills in the internal chamber. Doing so would release the air pressure from the annular space of the air bladder, which would trigger the tablet destruction mechanism thereby rendering the medication unusable.

A pharmacist may fill the prescription through slits at the top of bladder 30. Once the prescription is filled, the pharmacist may seal the device with a lid. The lid contains glue that is covered by a seal that the pharmacist removes when s/he is about to seal the device. This way, the silts cannot be accessed without removing the lid, which will cause the air bladder to rupture and depressurize since they are glued together.

There is a small passageway 32 through the doubled-walled air bladder 30 that will allow tablet dispensing via key 12 (FIG. 1). This opening or passageway 32 is covered by key 12, which also completes an electrical circuit of an internal clock in preparation to retrieve and dispense a next tablet. Once key 12 is inserted in passageway 32, it will remain in the opening with the help of a one-way hooks/latches attached to its sides. Key 12 can slide back and forth to gain access to the tablet. If the key is forcibly removed, it will rupture the air bladder 30 thereby triggering the destruction mechanism and preventing tampering through opening 32.

Air bladder 30 comes pressurized from manufacturer, the pharmacist only pushes in the tablets through the slits at top and when done, seals it with the lid. Air bladder and encasement can be a single piece for more compact size, with hard plastic on the outside and inflatable plastic or rubber on the inside. Air bladder will surround the medication chamber except for medication feeding and ejection slits. The feeding slits must not allow tablets to exit through it. The ejection slit must not allow manual tampering with the dispensing mechanism. The ejection channel may be covered with an extension from the air bladder to activate. The feeding and the ejection slits must not allow entry of any object that might hinder the trigger mechanism, or grinding mechanism. Placing slits horizontally at the top of the container, and/or sealing the feeding slits after inserting medication. The loss of pressure within the air bladder 30 enables a spring to overcome the pressure in air bladder, leading the grinding mechanism to trigger. Having an extension of the air bladder within the container pressing against the trigger mechanism would prevent the application of outside pressure that might hinder the triggering mechanism.

Triggering Mechanism

Pills are contained in a chamber enclosed by the pressurized bladder 30. The triggering mechanism is activated upon tampering with (breaking into) the housing, which causes loss of bladder pressure and engagement of a spring-loaded shaft with a pre-loaded coil spring which, in turn, spins the shaft to grind the pills and/or release other substances that mix with the ground pills. They key does not affect the air bladder pressure unless it is pulled aggressively from the outside after initial insertion.

The triggering mechanism has a spring that presses against the air bladder. The trigger mechanism can release the potential energy to move the grinding bits, which will turn release the activated charcoal and/or naltrexone by rupturing the thin membrane surrounding the central medication containing chamber, and/or grinding the solid naltrexone pills contained therein, and/or permitting the release of fluid by pulling apart a sealed soft plastic container]. The trigger mechanism could be used to release the fluids directly from the containers instead of the grinding bits. Releasing fluids first with a delay in grinding would allow tablets to become softer, allowing for better grinding, mixing, and more efficiently reduce the bioavailability of the medication in the tablets.

Figure 4A:
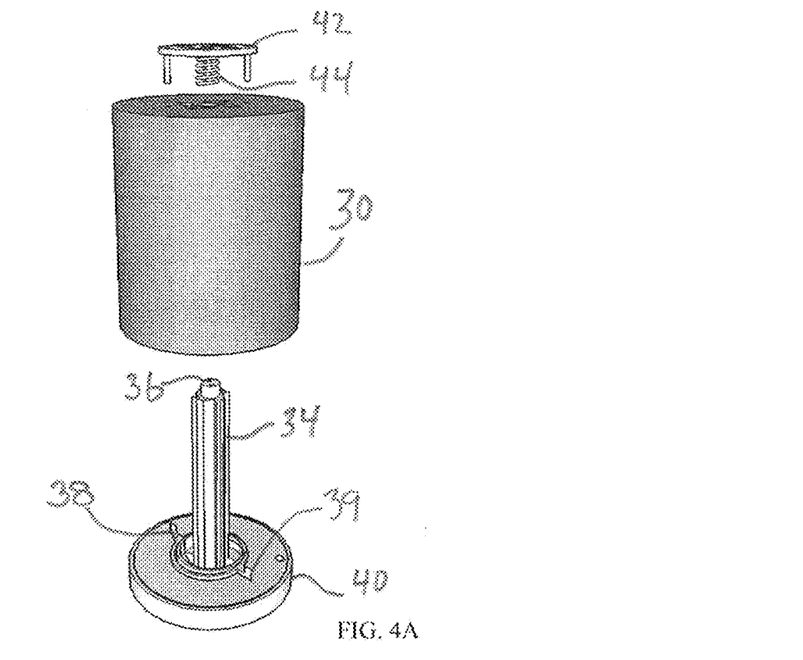
FIGS. 4A and 4B show an exemplary grinder chamber inside the container, which is encased by an expandable or rubber bladder.
Figure 4B:
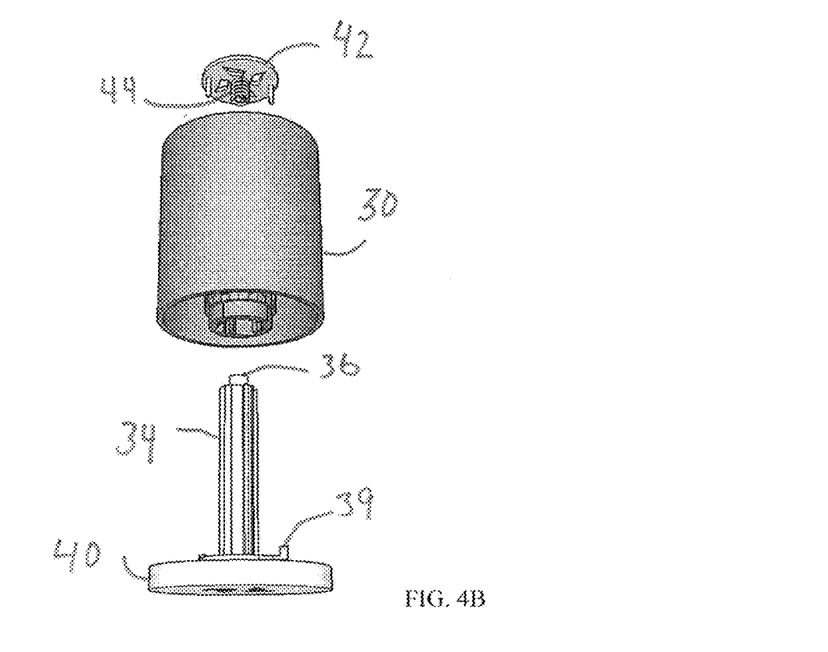
Figure 5A:
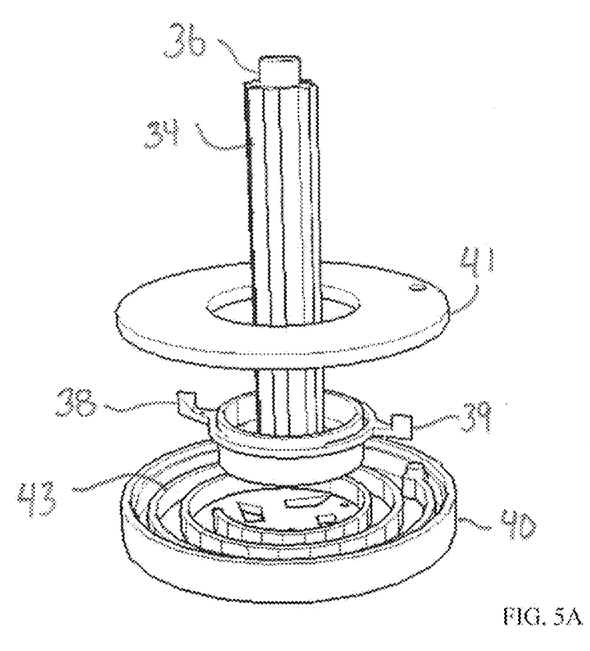
FIG. 5A shows an exploded view of the grinding or pill destruction mechanism.

FIGS. 4A and 4B show an exemplary grinding chamber inside the container 10 and encased by the bladder 30. Also shown is a spring loaded locking mechanism comprising four downward oriented rods 34 positioned around a shaft 36 that prevent rotation of shaft 36 when positioned in a normal position. Shaft 36 also couples rupturing fins 38, 39 and extends through housing 40 embodying a pre-loaded helical or coil spring ring 43 (FIG. 5A). A trigger plate 42 at the top of shaft 36 is biased via spring 44 to prevent activation of grinding action during normal usage of the medicinal container. If bladder 30 is punctured during any attempted tampering, bladder 30 collapses thereby causing engagement and spinning of shaft 36 to destroy contents of the internal chamber.

Once the tablets are inserted in the feeding slits, they will pile up in the spaces between the grinding bits. The grinding bits will move once the triggering mechanism releases the potential energy. The potential energy could be from a pre-loaded spring or other mechanism, e.g., a motor-controlled grinder or chopper. The size of the grinding bits will depend on the formulation of the prescription for the applicable medication. The grinding bits should be mesh-like with a minimum possible thickness to allow better mixing of the ground tablets and substances such as activated charcoal and/or naltrexone. The movement of the grinding bits could be used to release the activated charcoal and/or naltrexone.

The invention may incorporate activated charcoal and naltrexone containers. The size of the container 10 size is also dependent on the treatment regimen. The container may be rigid or inflatable. Activated charcoal suspension may be homogenized by adding clay powder and sorbitol to prevent the settling thereof and a surfactant to increase the efficacy of the destruction of the tablets structural integrity]. Homogeneity of the suspension should be balanced with its viscosity to promote the dissolution of opioids or other medication in the suspension. Sorbitol also has the benefit of preventing freezing of the activated charcoal suspension. The amount of naltrexone will depend on the [prescription details identified] above.

Figure 5B:
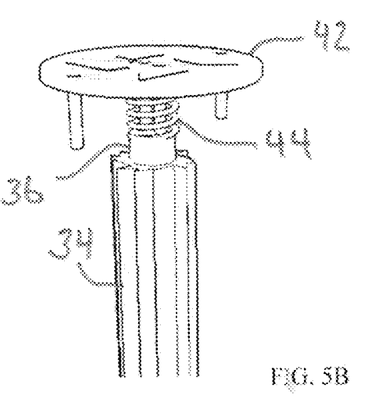
FIG. 5B shows a portion of a trip mechanism that activates grinding of container contents.

FIG. 5A shows an exploded view of the grinding or pill destruction mechanism comprising shaft 36, rods 34, fins 38, 39 and housing 40 and cover plate 41 embodying preloaded spring 43. The internal surface of grinding chamber may be coated with abrasive texture/material to assist in pill destruction. FIG. 5B shows plate 42 and biasing spring 44 to displace plate 42 against the bladder during normal operation.

Figure 6:
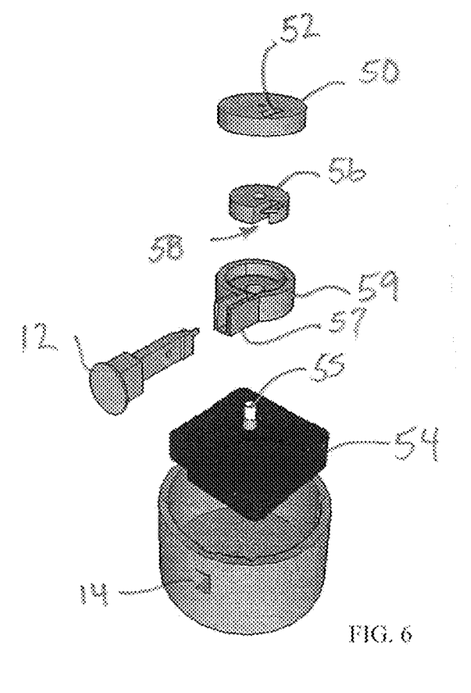
FIG. 6 shows an exploded view of dispensing mechanism for opioids or other controlled drugs.

FIG. 6 shows an exploded view of the dispensing mechanism. This includes a rotating disc 50 with one slit 52 to allow medication to fall through. Disc 50 is attached to clock shaft 55 of minutes/seconds rotational axis of clock 54. Dispensing disc 56 with channel slot 59 is for medication to enter after being released by disc 50. Medication containment chamber 58 holds medication in place until removal of key 12 thereby permitting a user to access a dose of medication at prescribed times determined by clock 54 that controls rotational axis 55.

Figure 7A:
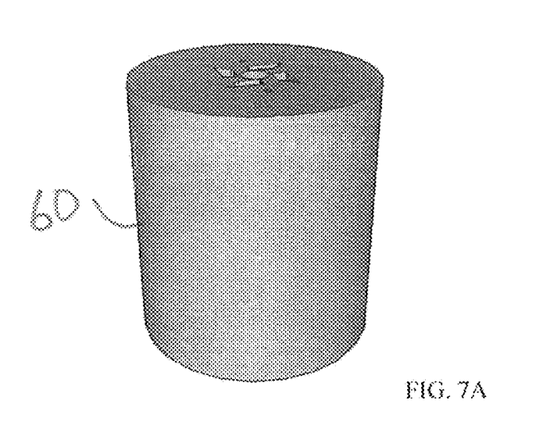
FIGS. 7A, 7B and 7C respectively show lateral, top and bottom views of the grinding chamber encased by the expandable or rubber bladder.
Figure 7B:
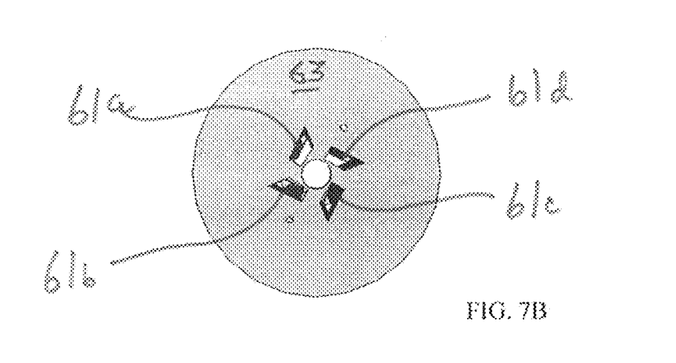
Figure 7C:
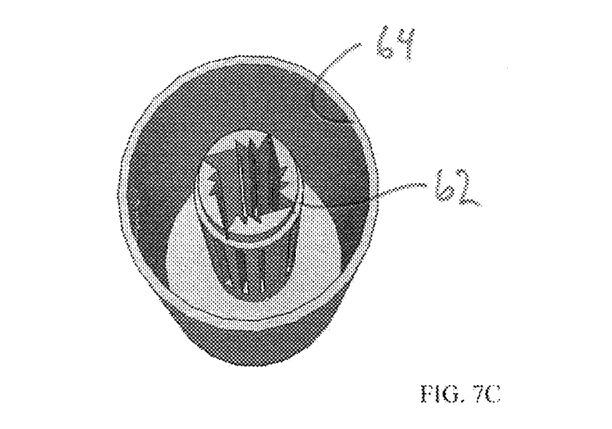

FIGS. 7A, 7B and 7C respectively show lateral, top and bottom views of the grinding chamber 60 encased by bladder 30. Four medication loading slits 61a, 61b, 61c and 61d are shown of top surface 63 of FIG. 7B including small openings for exterior locking rods that prevent rotation of grinding baffle 62 (FIG. 7C) that is triggered by loss of pressure in annular air bladder 30. Bottom view of FIG. 7C depicts details of the grinding baffles 62 that spin when triggered. Interior walls 64 of the grinding chamber may be coated with abrasive material to facilitate more efficacious and rapid grinding of contents by the rotational forces once the mainspring locking mechanism 43 (FIG. 5) is triggered via activation of anti-tampering air bladder. Activation may also occur upon application of catastrophic vertical or horizontal force to external encasement (e.g., when the container is placed in a hydraulic press, crushed by a vehicle, placed in a vice, etc.) and which remaining volume will be filled with a chemical solution contained in a thin plastic membrane/bag in a quantity sufficient to offset a possible overdose caused by, or the sought after euphoric effects resulting from the abuse, misuse or attempting use contrary to prescription instructions of, the active amount of medication prescribed and contained in the device.

Figure 8A:
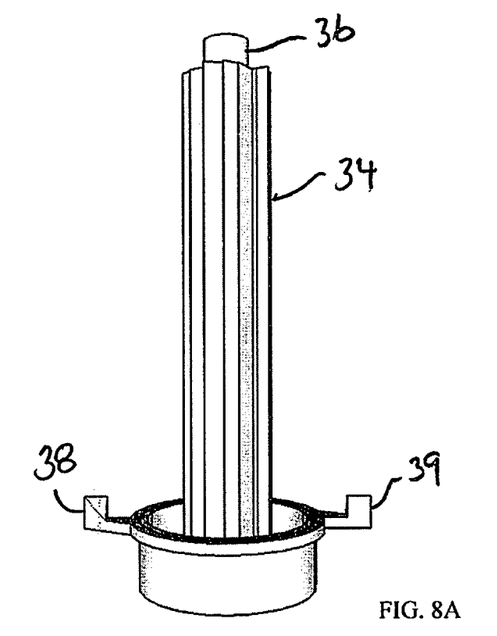
FIGS. 8A, 8B and 8C show a central shaft, locking rods and rupturing/grinding fins in greater detail.
Figure 8B:
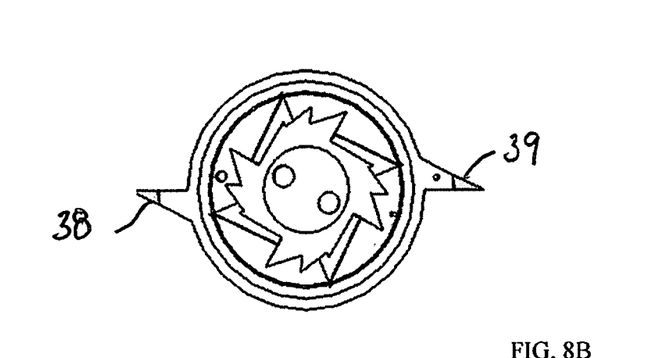
Figure 8C:
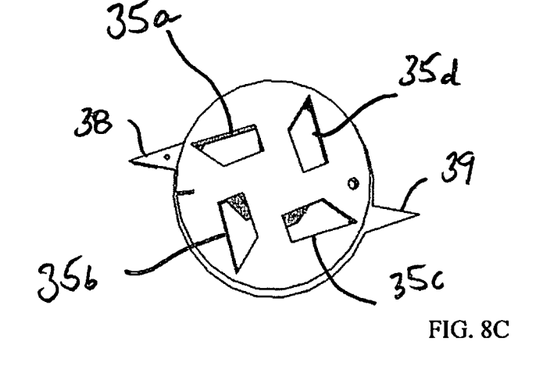

FIGS. 8A, 8B and 8C show the central shaft 36, rods 34 and rupturing/grinding fins 38 in greater detail, as well as top and bottom views of the overall grinding mechanism. Locking slots 35a, 35b, 35c and 35d for rods 34 are also shown. These provide insertion holes for central locking rods 34.

Figure 9A:
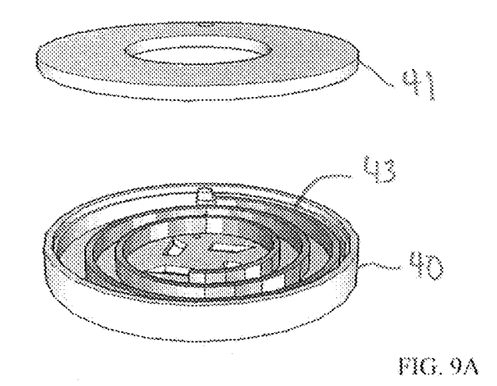
FIGS. 9A, 9B and 9C show perspective, top and bottom views of coil spring casing that embodies the pre-loaded coil spring.
Figure 9B:
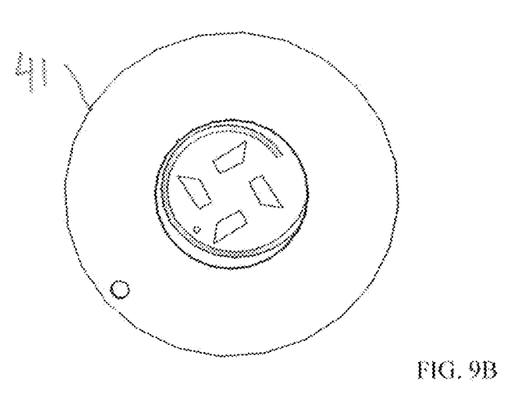
Figure 9C:
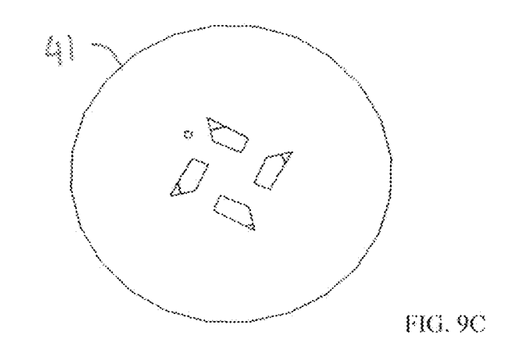

FIGS. 9A, 9B and 9C show perspective, top and bottom views of coils spring casing 40 and cover plate 41 that embodies the pre-loaded coil spring 43.

Figure 10A:
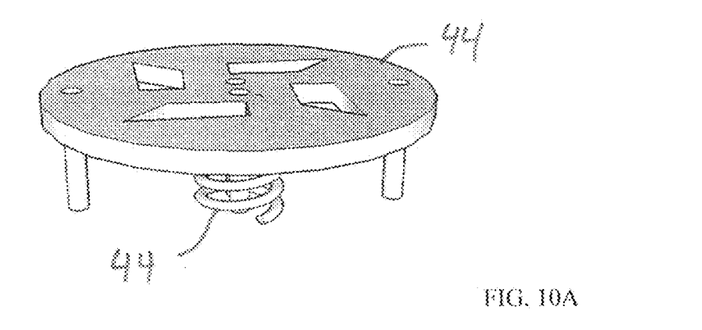
FIGS. 10A, 10B and 10C show perspective top and bottom views of the spring-loaded plate that interlocks with locking rods.
Figure 10B:
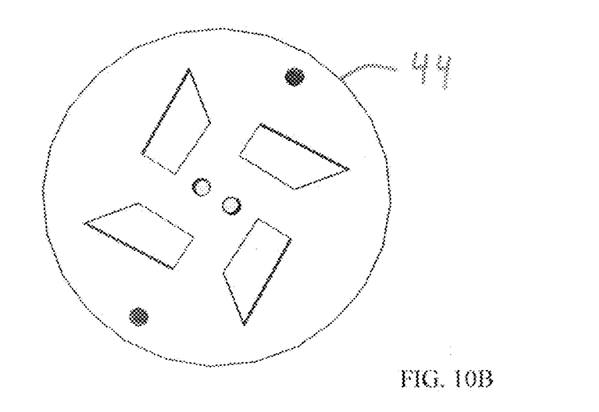
Figure 10C:
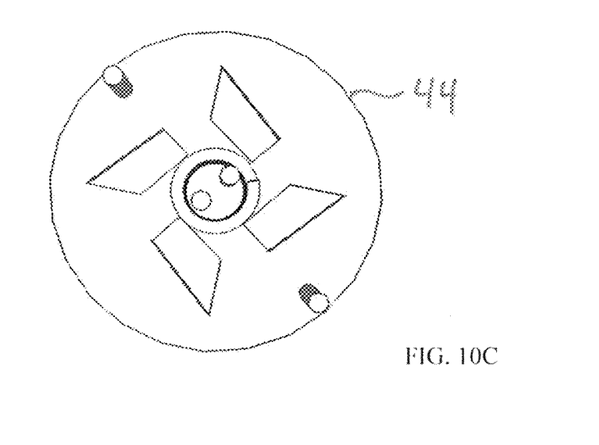

FIGS. 10A, 10B and 10C show perspective, top and bottom views of the spring-biased plate 42 that couples shaft 36 and locking rods 34.

Figure 11A:
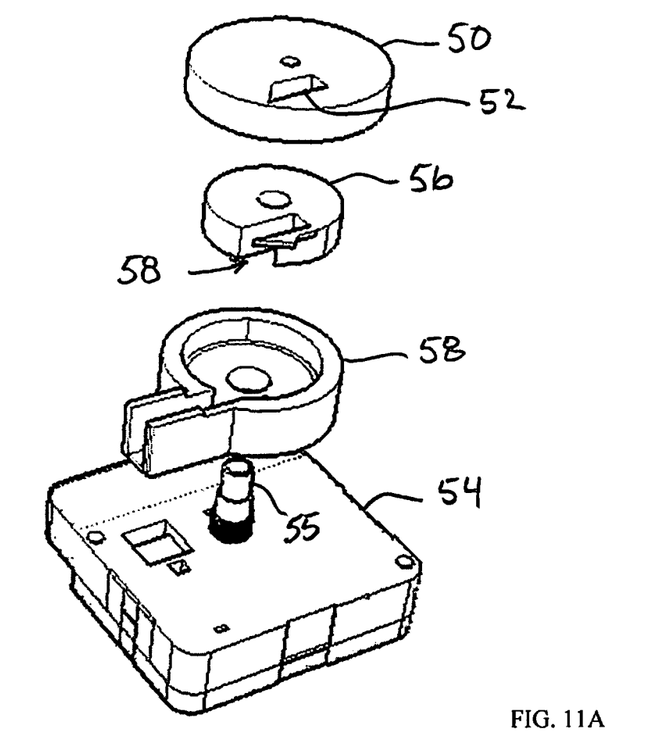
FIG. 11A shows an exploded view of an exemplary dispensing mechanism in functional relationship, which includes rotating disc coupled to a clock shaft to select a pill through a drop-down hole, dispensing disc, containment chamber, clock and key chute.
Figure 11B:
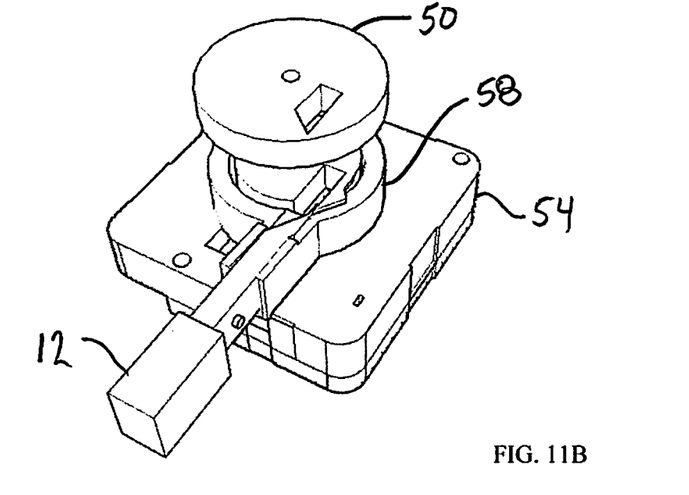
FIG. 11B shows elements of FIG. 11A in assembled relationship.

FIG. 11 shows the dispensing mechanism in functional relationship, which includes rotating disc 50, dispensing disc 56, containment chamber 58, clock 54 and key 12. An inexpensive motor like that of a quartz clock can act as both for timing and moving pills. The speed of the quartz clock can be adjusted electronically to change the rate of dispensing. The dispensing time may be slightly lower than the prescription dosage, which prevents accumulating delay of release of future dispensing. For example, if a patient is supposed to take a tablet at noon but instead takes it at 12:20 pm, the next tablet can only be taken at 12:20 am. This way, the time at which a person can dispense the medication will increase cumulatively every time the person delays taking their medication. If dispensing time was 11 hours instead, for example, this effect would be less noticeable.

Dispensing may be gravity-dependent when the device is positioned upward, or dispensing may be fed from a spring-loaded magazine containing multiple tables. The hours/minutes'/seconds' hand[s] would rotate to dispense a tablet according to a prescribed schedule. The tablet in dispensing position prevents any further tablets from getting in, until the tablet drops into a chute for retrieval by the user.

Once in the hour hand, device orientation is not essential for dispensing. The hour hand will rotate till it reaches 12 O'clock and will be stopped by a key inserted through the ejection slit. The key has a latch mechanism that prevents the clock from rotating any further. Removing the key would allow the removal of the tablet by the person. When the key is reinserted, the latching mechanism will not work until the hours' arm makes a full revolution for the next tablet to be dispensed.

The key has to be inside the ejection channel for the clock to continue working. This is done by placing electrically conductive pins inside the key that complete the clock's circuit, preventing continuous automatic dispensing. The pins slide into conductive grooves within the ejection channel walls, making it next to impossible to complete the clock's circuit by placing metal within the ejection channel. The placement of the pins could be unique to several hundred/thousand devices. With an appropriate distribution of devices, this will create a relatively unique key for each device, allowing further security and new device delivery possibilities.

Instead of a quartz clock, a motor connected to a circuit with a refractory period of eleven hours, for example, would allow similar functionality. The refractory period could be achieved solely electronically or with a microprocessor (digitally). The key can have a pushbutton that will initiate dispensing. A microprocessor would enable more functionality, such as more flexibility with dispensing, sending and receiving information, and a dual-functioning bottle containing both a regular prescription and as required prescription.

The invention may incorporate display and notification. One may use the key insertion to start a countdown timer digital display with an alarm that sounds when it is time to dispense. One may also add an electronic counter to the display that counts adds one every time the key is inserted/removed. These could be done with all three dispensing mechanism described above. Using a microprocessor, we can add digital functionality such as smartphone notification and data collection.

In addition to prescription formulated opiates, the invention contemplates use with other Scheduled and Non-Scheduled drugs or abused or potentially abused substances, such as amphetamines, dextroamphetamines, barbiturates, benzodiazepines, sedative-hypnotics (e.g., Ambien), antidepressants, methadone and combinations thereof.

Figure 12A:
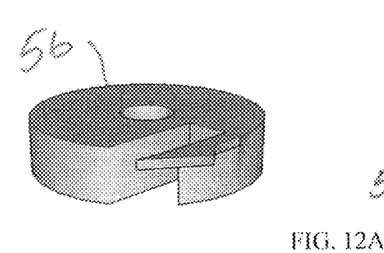
FIGS. 12A, 12B and 12C shown perspective, top and bottom views of an exemplary dispensing disc of FIGS. 11A and 11B.
Figure 12B:
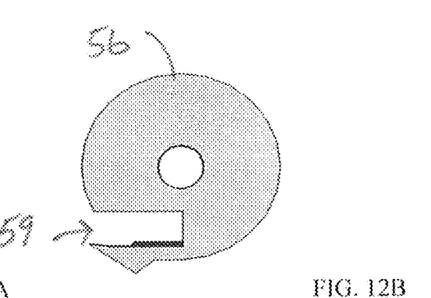
Figure 12C:
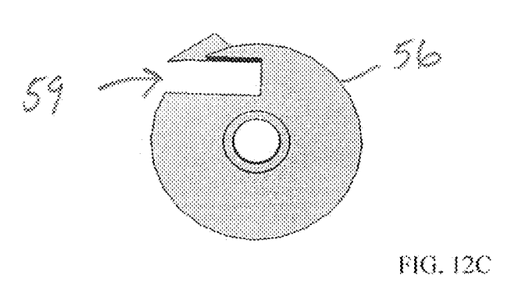

FIGS. 12A, 12B and 12C show perspective, top and bottom views of dispensing disc 56 having a dispensing chute 69 to dispense a tablet.

Figure 13:
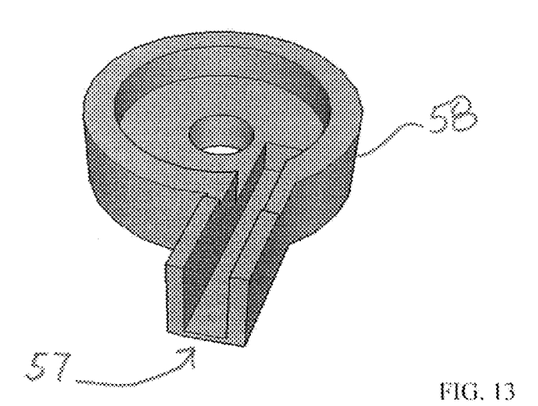
FIG. 13 shows a perspective view of containment chamber having an internal pill chamber and chute that receives key and dispenses a pill.

FIG. 13 shows a perspective view of containment chamber 58 having an internal chamber and chute 57 that receives key 12 to retrieve an opiate pill. Chamber 58 includes conductive metallic elements (not shown) that mates with corresponding electrical circuit elements on key 12 to activate or power clock 54 to engage movement of a central axis in accordance with the dispensation timing in order to provide timed release of medication.

Figure 14A:
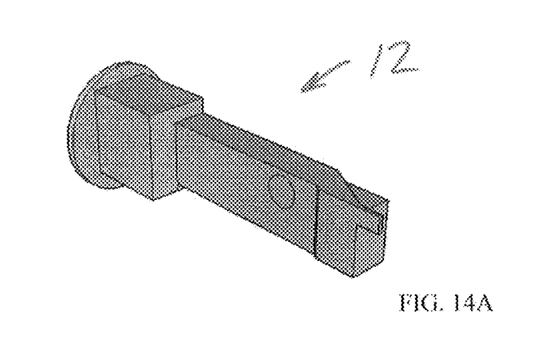
FIGS. 14A and 14B show perspective and side views of exemplary key having a circuit element to complete a circuit that activates/deactivates the clock of FIGS. 11A and 11B when inserted/removed from the chute of FIG. 13.
Figure 14B:
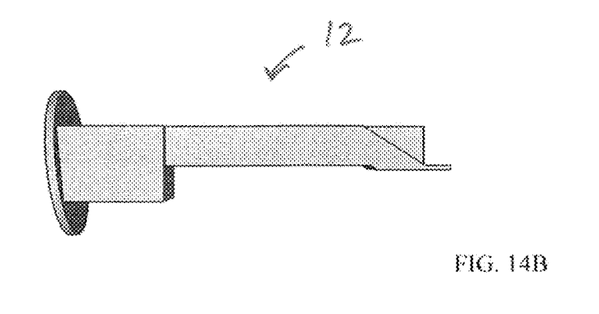

FIGS. 14A and 14B show perspective and side views of key 12 having an electrically conductive circuits on the surface thereof (not shown) which, upon removal of the key, pauses or stops the clock 54 thereby preventing the further dispensation of medication in excess of a single dose in accordance with the prescription timing when the key is removed.

The foregoing description details an illustrative embodiment of the invention, which is not limited to the specific elements set forth herein. As known in the art, elements of the illustrative embodiment may be modified or altered by known methods or substituted elements that perform the same or similar function without departing from the scope of the invention. Thus, it is not intended that the description provided herein serve as a limitation of the invention, but instead, the invention includes such modifications and alterations as may come to those skilled in the art. The scope of the invention is thus defined by the appended claims.

We claim:

1. A tamper-proof medicinal container comprising:
(a) an outer housing having a lid that permit insertion of pills,
(b) an inner chamber for holding discrete quantities of said pills,
(c) a dispensing section to provide timed dispensing of said pills from said inner chamber according to a timing device preprogrammed according to a dosage regime,
(d) a pill destruction section to destroy or adulterate said pills upon activation, and
(e) a pressurized double-walled bladder forming an annular chamber surrounding the inner chamber, dispensing section and/or pill destruction section being operative to depressurize and activate said pill destruction section upon tampering with said outer housing.

2. The tamper-proof medicinal container of claim 1, wherein said pill destruction section comprises a pre-loaded coil spring that spins a shaft to effect grinding of said pills.

3. The tamper-proof medicinal container of claim 2, wherein said pill destruction section further effects release of a substance to adulterate said pills with a foul taste, color, odor or other undesirable property to deter consumption by a user.

4. The tamper-proof medicinal container of claim 3, wherein the substance comprises an FDA approved generically available opioid antagonist.

5. The tamper-proof medicinal container of claim 3, wherein the substance comprises a non-toxic admixture of activated charcoal suspension, sorbitol or other chemical effective in lowering the freezing temperature of fluids, kaolin clay, multi-sensory deterrent and a surfactant.

* * * * *